US00PP08668P

United States Patent [19]

van Andel

[11] Patent Number: Plant 8,668

[45] Date of Patent: Mar. 29, 1994

[54] ALSTROEMERIA NAMED STAGELMI

[75] Inventor: Jacob van Andel, Aalsmeer, Netherlands

[73] Assignee: Van Staaveren BV, Aalsmeer, Netherlands

[21] Appl. No.: 25,581

[22] Filed: Mar. 3, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Tilton, Fallon, Lungmus & Chestnut

[57] ABSTRACT

A new and distinctive Alstroemeria cultivar particularly distinguished by its profuse and recurrent production of medium sized flowers having six petals arranged in two concentric circles of three petals per flower; The new cultivar having lemon yellow coloration for its outer petals and indian yellow coloration for the body of the inner petals and lemon yellow coloration for the base of the inner petals. The petals including numerous longitudinal chrysanthemum crimson stripes. These flowers being carried on erect stems branching from a tall main stem forming a strong upright bush.

1 Drawing Sheet

BACKGROUND OF THE NEW PLANT

This Alstroemeria cultivar originated as a seedling hybrid produced in my nursery at Aalsmeer, The Netherlands, by my crossing of two plants selected from a field of various Alstroemeria varieties maintained at my nursery for breeding purposes. This particular seedling was selected from those produced by the hybrid because of its ability to produce in winter. This selected seedling was propagated by me at Aalsmeer by dividing root stock with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new Alstroemeria plant as observed from plants grown under greenhouse conditions in Aalsmeer, The Netherlands, with the stated flower colors being according to The R.H.S. Colour Chart of The Royal Horticultural Society of London, England.

THE PLANT

Origin: Seedling.

Parentage:

*Seed parent.*—80 G 377-4 (unpatented). Yellow color.

*Pollen parent.*—83 G 416-3 (unpatented). Yellow color.

Both of these parent plants are so identified in my business records maintained at the office of my nursery at Aalsmeer, The Netherlands and the production of the aforementioned seedling are also recorded therein. The parent plants are proprietary. Also, both parent plants are hybrids.

Classification:

*Botanic.*—*Alstroemeria hybrid.*

*Commercial.*—Alstroemeria hybrid.

Form: An upright bush.

Height: About 150–200 cm.

Growth rate: Flowering in about 3–4 months following the first planting.

Main stem length: 150–200 cm.

Strength: Strong.

Branching character: The main stem has an umbel in which 3–5 branches (peduncles) are grouped. At the end of the peduncle a flower is situated on a pedicel. Above the peduncle additional pedicels may occur. The number of flowers per branch is 2–3.

Growth: vigorous.

Foliage:

*Quantity.*—Abundant.

*Number of leaves.*—25–30.

Size and shape of leaf.—The leaf is elliptical shaped, about 12–16 cm in length and about 2–3 cm in width.

Margin type.—Entire.

*Texture.*—Glossy.

*Color.*—Upper side — 137A. Under side — 137C.

Rhizomes: Yes.

*Color.*—RHS 155D.

*Size.*—10–30 cm.

THE BUD

Size:

*Diameter.*—1–2 cm.

*Length.*—2–3 cm.

Shape: Pear-shaped (long).

Rate of opening: Bud to flower in about 3–5 days.

Color of petals:

*When sepals first divided.*—RHS 13B.

*When petals begin to unfurl.*—RHS13B.

Slitting: No.

THE FLOWER

Blooming habit: Recurrent and profuse — Spring and Fall.

Size of bloom: Medium.

*Diameter*—5-6 cm.

*Depth.*—4 cm.

Borne: Singly

Shape: When bloom first opens and when it matures the blooms are cup shaped.

Petalage:

*Number of petals.*—Six.

*Arrangement.*—Two concentric circles of three petals.

*Texture.*—Minutely crinkled or creped.

*Form.*—The three outer petals are both lobed at the apex and the inner three petals are substantially obovate with a characteristic slightly involute wave on each side of each inner petal space from the apex which can make the inner petals appear to be lobed in shape.

*Margin type.*—Straight.

*Apex.*—Pointed.

*Appearance.*—Velvety.

*Remain on stem.*—Three weeks.

*Color.*—Outer petals Body: RHS 13B. Base: RHS 13B. Reverse side: RHS 13B. Inside petals Body: RHS 17B. Base: RHS 13B. Reverse side RHS 17B.

*Stripes.*—10-30 per inner petal. Color: 185 A.

Discoloration after full bloom: Slightly.

Persistence: The petals of matured flowers do not hang on and dry.

Fragrance: None.

Lasting quality:

*On the plant.*—About 3 weeks.

*As a cut flower.*—About 2 weeks.

Flower stem:

*Length.*—About 12-15 cm.

*Character.*—Upright and strong.

*Color.*—RHS 137B.

THE REPRODUCTIVE ORGANS

Stamens:

*Number.*—About Six.

*Arrangement.*—Clustered around the style.

*Anthers.*—Size: 8-10 mm. Color: RHS 7A.

*Filaments.*—About 5 cm. Color: RHS 25A.

*Pollen.*—Color: RHS 13A.

Pistils:

*Number.*—One.

*Styles.*—Length about 4-5 cm (RHS 25B).

*Stigmas.*—RHS 12B.

Fruit:

*Fertile.*—Yes.

*Shape.*—Round.

*Color.*—RHS 163A.

I claim:

1. A new and distinctive Alstroemeria plant, substantially as herein shown and described.

* * * * *

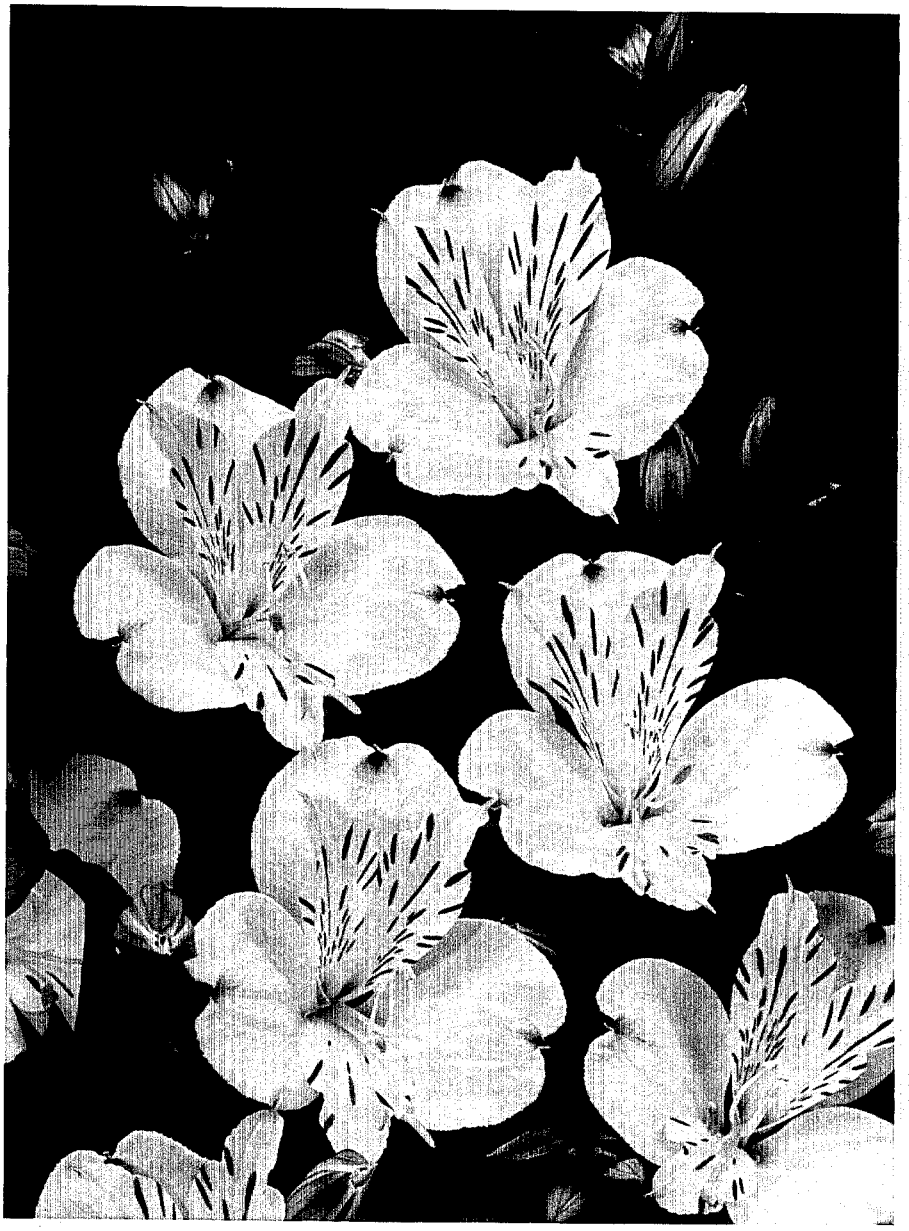

UNITED STATES PATENT AND TRADEMARK OFFICE

CERTIFICATE OF CORRECTION

PATENT NO. : PP 8,668

DATED : March 29, 1994

INVENTOR(S) : Jacob van Andel

It is certified that error appears in the above-indentified patent and that said Letters Patent is hereby corrected as shown below:

Column 3, line 22, delete "straight" and insert -- very finely dentate--.

Signed and Sealed this

Fifteenth Day of November, 1994

*Attest:*

*Attesting Officer*

BRUCE LEHMAN

*Commissioner of Patents and Trademarks*